United States Patent
Gherardi et al.

(10) Patent No.: US 10,987,701 B2
(45) Date of Patent: Apr. 27, 2021

(54) SORTING OR CLASSIFYING APPARATUS

(71) Applicant: BÜUK LIMITED, London (GB)

(72) Inventors: David Gherardi, London (GB); Benedict Deefholts, London (GB); Robert James Neil McLean, London (GB); Ben Ward, London (GB); Howard Myer, London (GB); Bill Saunders, London (GB); Saliya Gunaratne, London (GB); Timothy Kelf, London (GB); David McCambridge, London (GB)

(73) Assignee: BÜHLER UK LIMITED, London (GB)

(*) Notice: Subject to any disclaimer, the term of this patent is extended or adjusted under 35 U.S.C. 154(b) by 0 days.

(21) Appl. No.: 16/313,675

(22) PCT Filed: Jun. 28, 2017

(86) PCT No.: PCT/EP2017/066070
§ 371 (c)(1),
(2) Date: Dec. 27, 2018

(87) PCT Pub. No.: WO2018/002185
PCT Pub. Date: Jan. 4, 2018

(65) Prior Publication Data
US 2020/0269285 A1   Aug. 27, 2020

(30) Foreign Application Priority Data
Jun. 28, 2016   (EP) .................................... 16176769

(51) Int. Cl.
*G01N 33/02* (2006.01)
*B07C 5/342* (2006.01)
(Continued)

(52) U.S. Cl.
CPC ........... *B07C 5/342* (2013.01); *G01N 21/251* (2013.01); *G01N 21/359* (2013.01); *G01N 33/02* (2013.01);
(Continued)

(58) Field of Classification Search
CPC ...... B07C 5/342; G01N 33/02; G01N 21/251; G01N 21/359; G01N 2021/3181; G01N 2201/0637; G01N 2021/3155
See application file for complete search history.

(56) References Cited

U.S. PATENT DOCUMENTS 5,440,127 A * 8/1995 Squyres ................ B07C 5/3422
                                                         250/341.8
6,784,996 B2   8/2004 Ikeda et al.
(Continued)

FOREIGN PATENT DOCUMENTS

CN   103561876 A   2/2014
CN   104368540 A   2/2015
(Continued)

OTHER PUBLICATIONS

International Search Report and Written Opinion for corresponding Patent Application No. PCT/EP2017/066070 dated Sep. 7, 2017.

*Primary Examiner* — Patrick H Mackey
(74) *Attorney, Agent, or Firm* — Renner, Otto, Boisselle & Sklar, LLP

(57) ABSTRACT

A sorting or classifying apparatus comprising an illumination device for providing illumination or foreground illumination, the illumination device comprising a reflector (61) which has a reflecting surface (63) providing a reflection envelope, a first light source (70) which is disposed in spaced relation in front of the reflecting surface (63) and provides light of a first spectral output to the reflecting surface (63) for reflection thereby and which first light source (70) comprises a plurality of light elements or (Continued)

incandescent lamps (72), wherein the light elements or lamps (72) are disposed on or near a focal axis (X) of the reflector (61), and a second light source (71) which is disposed in spaced relation in front of the reflecting surface (63) and provides light of a second spectral output, different to the first spectral output to the reflecting surface (63) for reflection thereby and which second light source (71) comprises a plurality of light elements or light-emitting diodes (LEDs) (75) arranged along at least one row (77a, b) which extends along the length of the reflecting surface (63) and is arranged in a direction substantially parallel to the focal axis (X) of the reflector (61), optionally the first light source (70) is a source of near infra-red (NIR) light and the second light source (71) is a source of visible-spectrum light.

16 Claims, 14 Drawing Sheets

(51) Int. Cl.
  *G01N 21/25* (2006.01)
  *G01N 21/359* (2014.01)
  *G01N 21/31* (2006.01)
(52) U.S. Cl.
  CPC ............ *G01N 2021/3155* (2013.01); *G01N 2021/3181* (2013.01); *G01N 2201/0637* (2013.01)

(56) References Cited

U.S. PATENT DOCUMENTS

| | | | | |
|---|---|---|---|---|
| 6,853,447 | B2* | 2/2005 | Goetz | B07C 5/342 |
| | | | | 356/237.1 |
| 7,339,660 | B1* | 3/2008 | Cohn | B07C 5/3427 |
| | | | | 209/581 |
| 8,152,347 | B2* | 4/2012 | Brukilacchio | G02B 19/0066 |
| | | | | 362/555 |
| 8,269,845 | B2* | 9/2012 | Fruehwirth | B07C 5/126 |
| | | | | 348/210.99 |
| 9,000,319 | B2 | 4/2015 | Deefholts | |
| 9,074,756 | B2 | 7/2015 | McLean | |
| 9,146,190 | B2 | 9/2015 | Hug | |
| 9,156,065 | B2 | 10/2015 | Hug | |
| 9,575,005 | B2* | 2/2017 | Balthasar | G01N 21/85 |
| 10,083,496 | B2* | 9/2018 | Peterson | G01B 11/04 |
| 10,099,258 | B2* | 10/2018 | Galbraith | B07C 5/342 |
| 10,288,594 | B2* | 5/2019 | Blanc | G01N 21/3563 |
| 2007/0045524 | A1 | 3/2007 | Rains, Jr. et al. | |
| 2007/0229832 | A1* | 10/2007 | Maeda | B07C 5/3416 |
| | | | | 356/419 |
| 2010/0103661 | A1 | 4/2010 | Chiou et al. | |
| 2011/0297590 | A1 | 12/2011 | Ackley et al. | |
| 2012/0097583 | A1 | 4/2012 | Berghmans et al. | |
| 2013/0126396 | A1 | 5/2013 | Jones et al. | |
| 2014/0333755 | A1 | 11/2014 | Adams et al. | |
| 2015/0377427 | A1* | 12/2015 | Richert | B07C 5/342 |
| | | | | 362/218 |
| 2017/0285353 | A1* | 10/2017 | Liu | G02B 5/201 |
| 2019/0047024 | A1* | 2/2019 | Bourely | B07C 5/342 |

FOREIGN PATENT DOCUMENTS

| | | |
|---|---|---|
| CN | 104941926 A | 9/2015 |
| DE | 10 2012 214 019 B3 | 11/2013 |
| EP | 0 146 299 A1 | 12/1984 |
| EP | 1 314 489 A2 | 11/2002 |
| EP | 2 411 947 A | 3/2004 |
| EP | 2 324 935 A1 | 5/2006 |
| EP | 2 085 154 A2 | 1/2009 |
| EP | 2 671 651 A1 | 6/2013 |
| JP | 2012/096211 A | 5/2012 |
| JP | 2015/078912 A | 4/2015 |
| WO | 1996/003226 | 2/1996 |
| WO | 2000/019546 | 4/2000 |
| WO | 2002/085547 A2 | 10/2002 |
| WO | 2013/021154 A2 | 2/2013 |
| WO | 2013/108962 A1 | 7/2013 |
| WO | 2015/056501 A1 | 4/2015 |
| WO | 2015/156722 A1 | 10/2015 |
| WO | 2017/044177 A1 | 3/2017 |

* cited by examiner

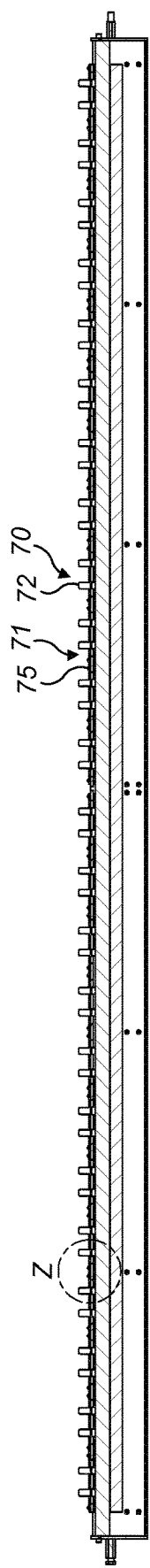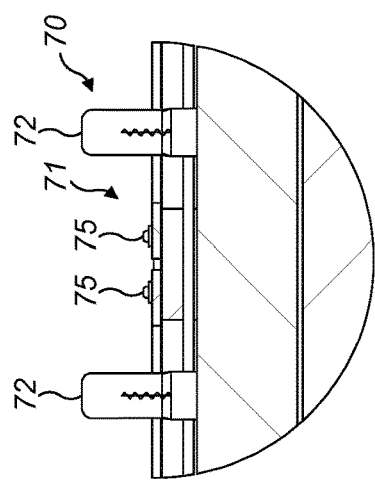
FIG. 6(e)
FIG. 6(f)

SORTING OR CLASSIFYING APPARATUS

The present invention relates to sorting or classifying machines, and illumination devices therefor, in particular for background or foreground illumination, especially in the sorting or classifying of particulate product, such as foodstuffs or vegetables.

Various illumination devices exist for providing background or foreground illumination in sorting or classifying machines, such as disclosed in EP-A-2324935, EP-A-2671651, CN-A0104368540, CN-A-104941926, GB-A-2411947, JP-A-2012/096211, JP-A-2015/078912, U.S. Pat. Nos. 6,784,996, 9,000,319, 9,074,756, 9,146,190, 9,156,065, US-A-2012/0097583, US-A-2013/0126396, US-A-2014/0333755, WO-A-2002/085547, WO-A-2013/021154.

It is an aim of the present invention to provide improved sorting or classifying machines, and illumination devices therefor, in particular for background or foreground illumination, especially in the sorting or classifying particulate product, such as foodstuffs or vegetables.

In one aspect the present invention provides a sorting or classifying apparatus comprising an illumination device for providing illumination or foreground illumination, the illumination device comprising a reflector which has a reflecting surface providing a reflection envelope, a first light source which is disposed in spaced relation in front of the reflecting surface and provides light of a first spectral output to the reflecting surface for reflection thereby and which first light source comprises a plurality of light elements or incandescent lamps, wherein the light elements or lamps are disposed on or near a focal axis of the reflector, and a second light source which is disposed in spaced relation in front of the reflecting surface and provides light of a second spectral output, different to the first spectral output to the reflecting surface for reflection thereby and which second light source comprises a plurality of light elements or light-emitting diodes (LEDs) arranged along at least one row which extends along the length of the reflecting surface and is arranged in a direction substantially parallel to the focal axis of the reflector, optionally the first light source is a source of near infra-red (NIR) light and the second light source is a source of visible-spectrum light.

In one embodiment (i) the reflector is an elongate, linear reflector, and optionally the reflecting surface is an elliptical surface; (ii) the first and second light sources are disposed within the reflection envelope of the reflector and in symmetrical relation to the reflector, thereby providing co-incident illumination of different wavelengths; and/or (iii) the first light source, optionally an incandescent light source, provides light with a wavelength of from about 400 nm to about 2.5 µm, and the second light source, optionally a light-emitting diode (LED) light source, provides light with a wavelength of from about 400 nm to about 780 nm.

In one embodiment the light elements or incandescent lamps are arranged along a single row.

In one embodiment the rows of light elements or light-emitting diodes (LEDs) are arranged in symmetrical spaced relation to the focal axis of the reflector, optionally the light elements or light-emitting diodes (LEDs) in the rows are offset in staggered relation along the length of the second light source.

In another aspect the present invention provides a sorting or classifying apparatus comprising a foreground illumination device for providing foreground illumination and an illumination box for providing background or reference illumination, the illumination box comprising a housing which includes an elongate illumination chamber having an illumination aperture, the illumination chamber comprising a first, rear surface and second and third, lower and upper surfaces which are disposed in spaced relation and extend forwardly from the rear surface to the illumination aperture and are disposed in substantially parallel relation, a light diffuser which is disposed at the illumination aperture and a light source which extends along a length of the illumination chamber, wherein at least one of the lower and upper surfaces, optionally both the lower and upper surfaces, has a first region and at least one second region which has different optical properties to optical properties of the first region such that the illumination box accommodates for variance in light generated by the light source and also for variance in light generated by the illumination device.

In one embodiment (i) the light source is an infra-red (IR) light-emitting diode (LED) light source with an emission spectrum within the near infra-red (NIR) and/or short-wave infra-red (SWIR) regions, encompassing wavelengths from about 700 nm to about 2.5 µm; (ii) the light source has an emission spectrum encompassing wavelengths from about 700 nm to about 2.5 µm; and/or (iii) the light source is disposed at or adjacent the rear surface, extending thereal-ong.

In one embodiment (i) the illumination chamber has a depth between the light source and the illumination aperture of less than 200 mm, preferably less than 150 mm, and most preferably less than 100 mm; (ii) the illumination chamber has a height between the lower and upper surfaces of less than 150 mm, preferably less than 120 mm, and most preferably less than 100 mm; (iii) the lower and upper surfaces have a diffuse finish and the housing provides an integrating box, or the lower and upper surfaces have a specular finish and the housing provides a mirror box; (iv) the lower and upper surfaces comprise a specular reflectance material or coating or a diffuse reflectance material or coating, optionally painted with white paint; and/or (v) at least one of the lower and upper surfaces has a plurality of second regions of different optical properties to the optical properties of the first region.

In one embodiment at least one of the lower and upper surfaces has a plurality of second regions of different optical properties to the optical properties of the first region, optionally; (i) at least one of the lower and upper surfaces has a pair of second regions of different optical properties to the optical properties of the first region, which are located to respective ones of rear and outward lateral sections of the at least one of the lower and upper surfaces, adjacent the light source; (ii) the second regions are spaced from one another by a distance; (iii) the second regions each have a length which is less than half of the length of the illumination chamber; and/or (iv) the second regions are substantially triangular in shape, and have a projection at the outer lateral edges of the illumination chamber, tapering inwardly to a central region of the illumination chamber, optionally the projection has a length of less than half of the depth of the illumination chamber, preferably less than one-third of the depth of the illumination chamber, and most preferably less than one-quarter of the depth of the illumination chamber.

In one embodiment (i) the first and second regions have a different surface color and/or a different spectral reflectance, optionally the first region being made of or coated with a diffuse reflectance material, such as optionally white paint and the at least one second region being made of or coated with low reflectance material, such as optionally black paint; and/or (ii) the first and second regions have different optical properties.

In one embodiment (i) the rear surface comprises a specular reflectance material or coating or a diffuse reflectance material or coating, optionally painted with white paint, or a low reflectance material or coating, such as optionally painted with black paint; and/or (ii) the rear surface has different optical properties to the lower and upper surfaces.

In one embodiment the illumination chamber further comprises fourth and fifth, side surfaces which define the lateral ends of the illumination chamber, optionally: (i) the side surfaces comprise a specular reflectance material or coating or a diffuse reflectance material or coating, optionally painted with white paint, or a low reflectance material or coating, such as optionally painted with black paint; and/or (ii) the side surfaces have different optical properties to the lower and upper surfaces.

In one embodiment the light source is an elongate light-emitting diode (LED) light source which comprises a plurality of light-emitting diodes (LEDs) spaced along a length thereof, optionally ones or groups of ones of the LEDs are of different wavelengths or colors, optionally selected ones or groups of ones of the LEDs can be controlled independently so as to control the pitch and/or intensity of the LEDs.

In a further aspect the present invention provides a sorting or classifying apparatus comprising an illumination device for providing background or reference illumination, the illumination device comprising a diffuser and an elongate light source which comprises a two-dimensional array of separated LEDs of a plurality of different wavelengths or colors, wherein the LEDs are arranged in substantially symmetrical relation to opposite sides of a longitudinal axis of the light source and the LEDs of each wavelength or color are connected to a common channel, such that the LEDs of one wavelength or color are switchable independently of the LEDs of other wavelengths or colors, such that a symmetrical illumination profile is provided.

In one embodiment (i) the LEDs are of three or more different wavelengths or colors; and/or (ii) the LEDs are arranged in a plurality of rows which extend in substantially parallel relation to the longitudinal axis of the light source, optionally the LEDs are arranged in three or more rows.

In a still further aspect the present invention provides a sorting or classifying apparatus comprising an illumination box for providing background or reference illumination, the illumination box comprising a housing which includes an elongate illumination chamber having an illumination aperture, the illumination chamber comprising a first, rear surface and second and third, lower and upper surfaces which are disposed in spaced relation and extend forwardly from the rear surface to the illumination aperture and are disposed in substantially parallel relation, and a light source which extends along a length of the illumination chamber, the light source being an infra-red (IR) light-emitting diode (LED) light source, optionally having an emission spectrum within the near infra-red (NIR) and/or short-wave infra-red (SWIR) regions.

'Optical properties' may comprise, for instance, spectral reflectivities, surface finishes, surface textures, scattering fractions (e.g. specular properties), scattering distributions, varying degrees of diffuseness and/or ratio of specular to diffuse reflectance.

Preferred embodiments of the present invention will now be described herein below by way of example only with references to the accompanying drawings, in which:

FIG. 6(e) illustrates a longitudinal sectional view (along section V-V in FIG. 6(c)) of the light assembly of the illumination device of FIG. 6(a);

FIG. 6(f) illustrates in enlarged scale a fragmentary longitudinal sectional view (detail Z, along section V-V in FIG. 6(c)) of the light assembly of FIG. 6(c)

FIGS. 1 and 2 illustrate a sorting machine in accordance with one embodiment of the present invention.

The sorting or classifying machine comprises a housing 1, a chute 2 which is supported by the housing 1 and to which a flow of particulate product is delivered, typically from an infeed vibrator, at least one detector 3a, b for detecting product as delivered on and/or from the chute 2, at least one background illumination device 4a, b for providing background or reference illumination to a field of view of the at least one detector 3a, b, and at least one foreground illumination device 5a-d for providing foreground illumination to a field of view of the at least one detector 3a, b.

Figure 1:
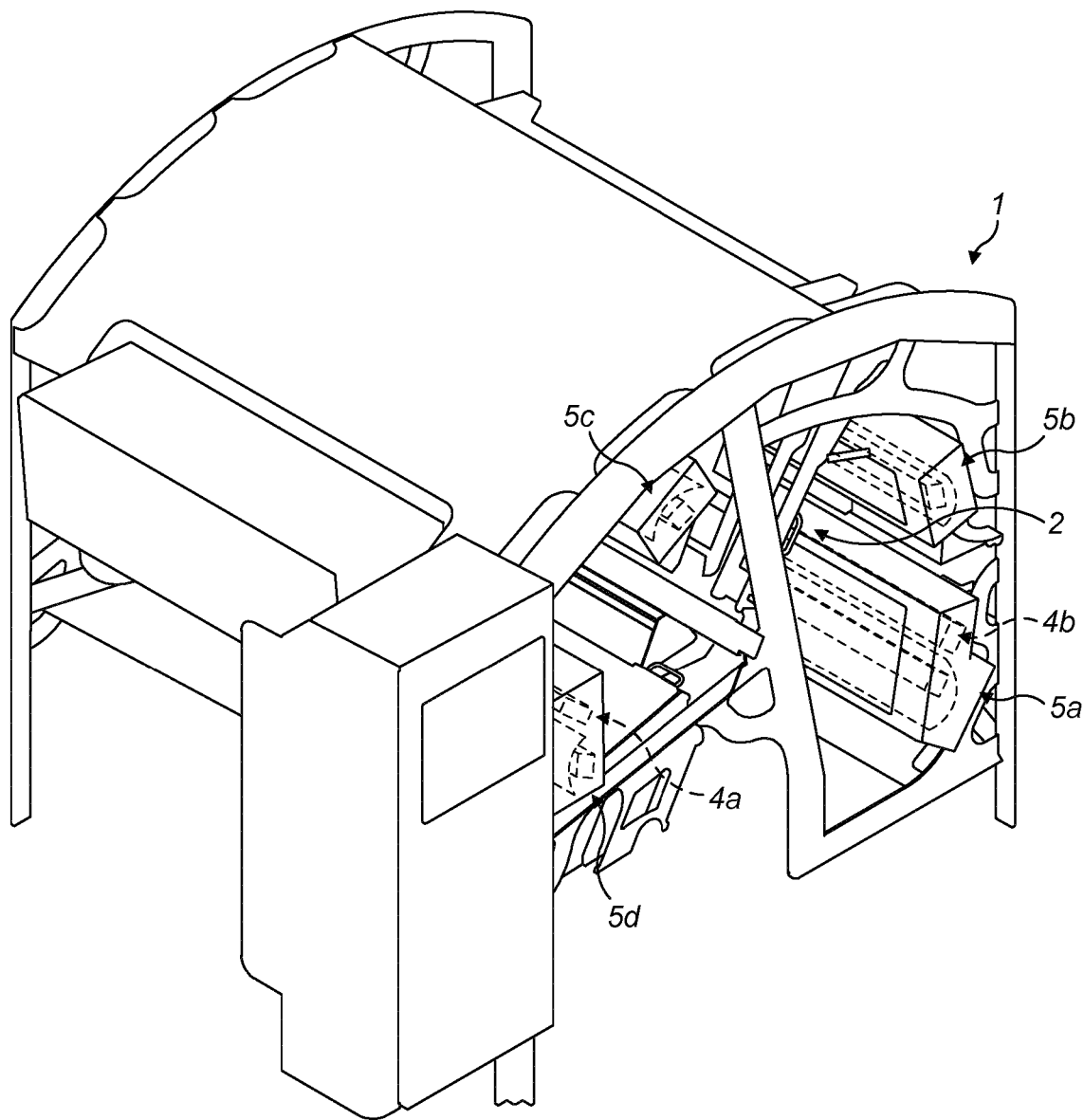
FIG. 1 illustrates a perspective view of a sorting or classifying machine in accordance with one embodiment of the present invention.
Figure 2:
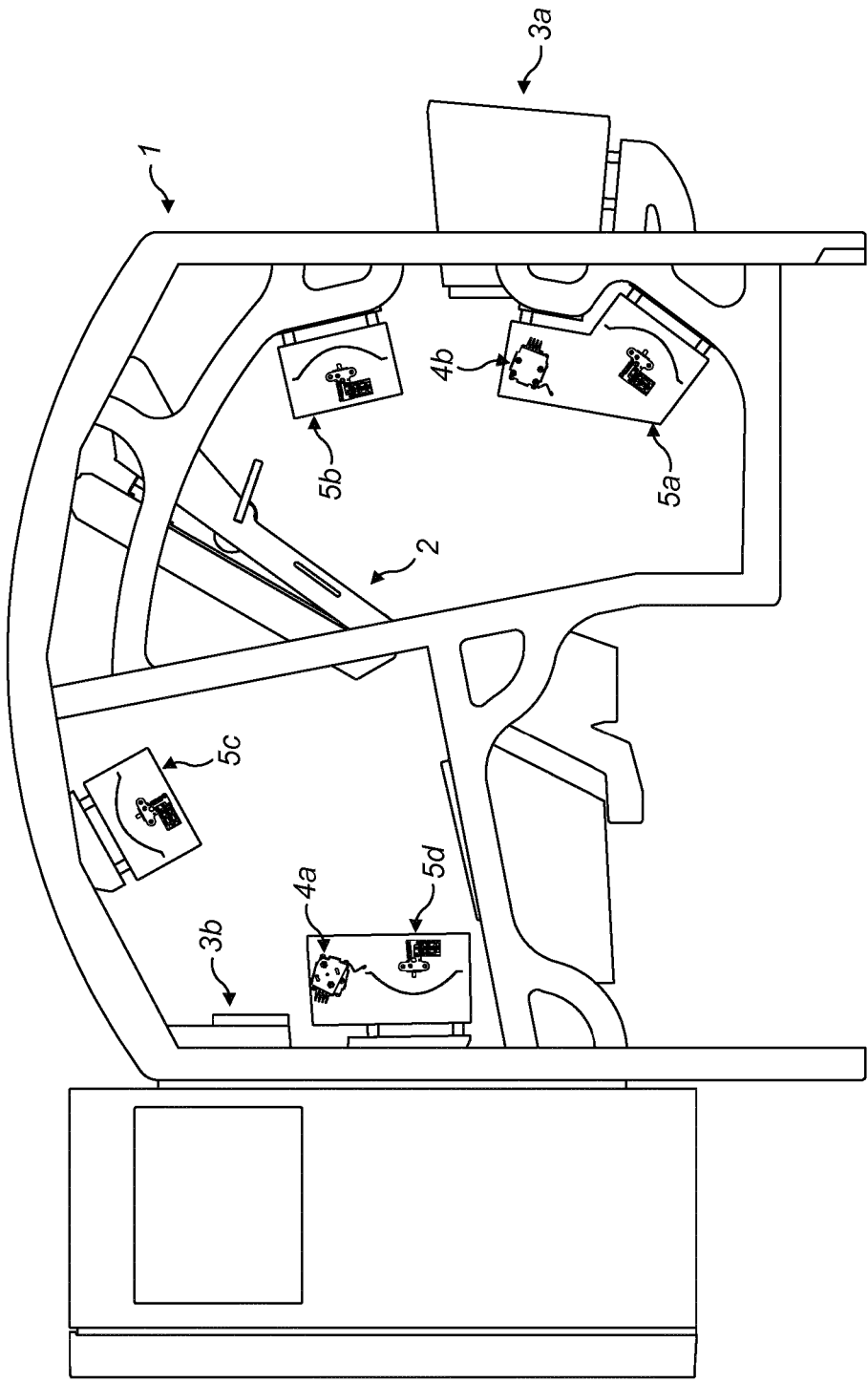
FIG. 2 illustrates a side view of the sorting or classifying machine of FIG. 1.
Figure 3A:
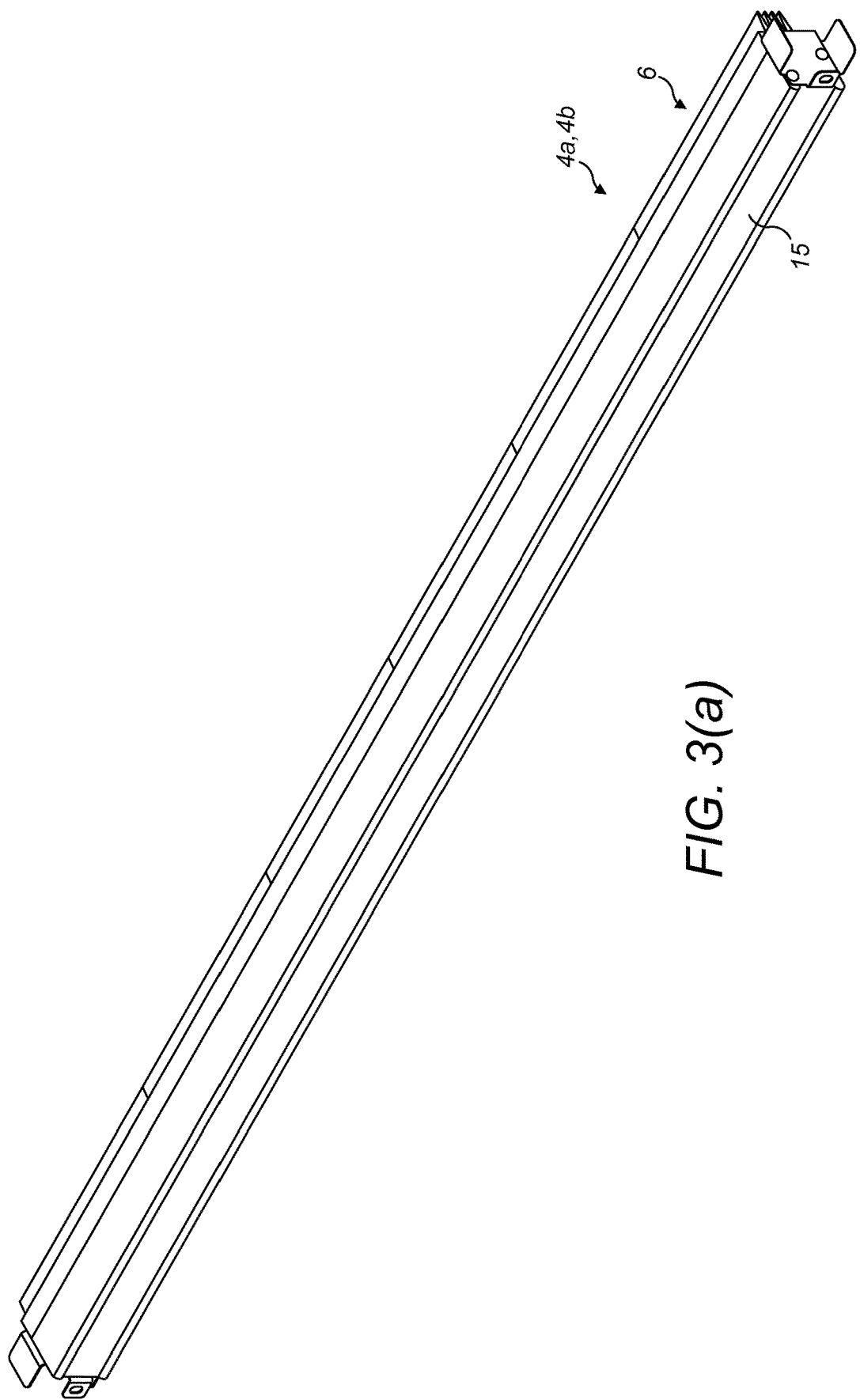
FIG. 3(a) illustrates a perspective view of a background illumination device in accordance with one embodiment of the present invention.
Figure 3B:
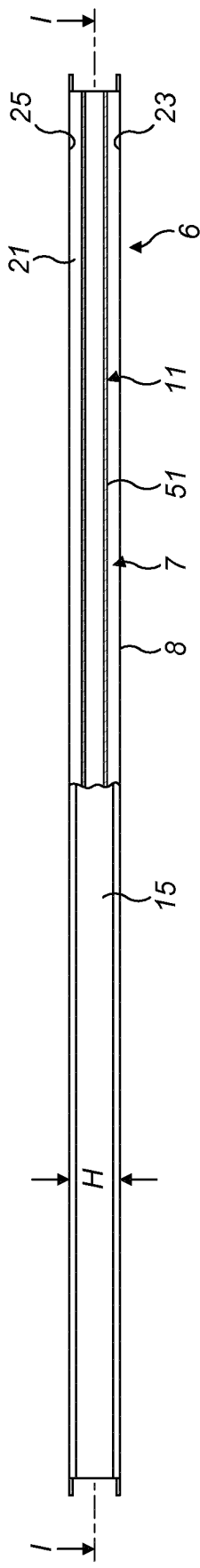
FIG. 3(b) illustrates a part cut-away front view of the illumination device of FIG. 3(a)
Figure 3C:
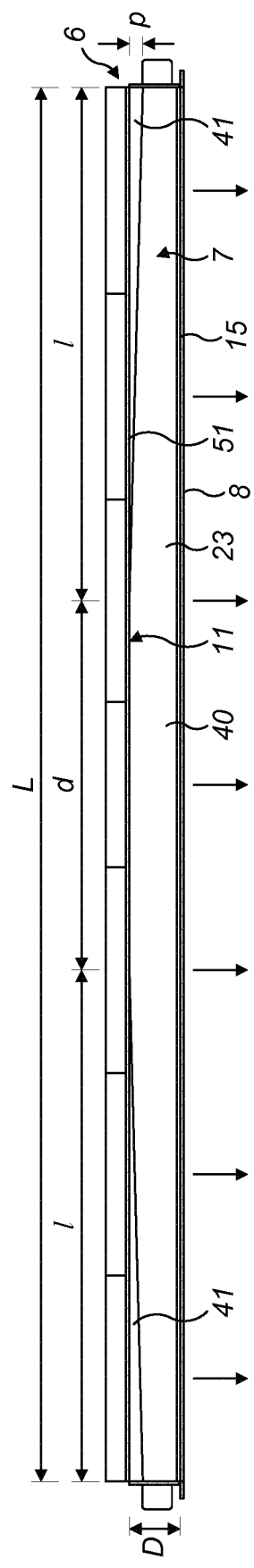
FIG. 3(c) illustrates a longitudinal sectional view (along section I-I in FIG. 3(b)) of the illumination device of FIG. 3(a)

FIGS. 3(a) to (c) illustrate a background illumination device 4a, b, for providing background illumination to the at least one detector 3a, b, in accordance with one embodiment of the present invention.

The illumination device comprises a housing 6 which includes an elongate illumination chamber 7, which has an elongate illumination aperture 8, a light source 11 which extends along a length of the illumination chamber 7, and a light diffuser 15 which is disposed at the illumination aperture 8 and diffuses the light thereat.

In this embodiment the illumination chamber 7 comprises a first, rear surface 21 and second and third, lower and upper surfaces 23, 25 which are disposed in spaced relation and extend forwardly from the rear surface 21 to the illumination aperture 8.

In this embodiment the illumination chamber 7 has a length L, here of 1800 mm.

In this embodiment the illumination chamber 7 has a depth D between the light source 11 and the diffuser 15, here of 70 mm.

In one embodiment the depth D is less than 200 mm, optionally less than 150 mm, and optionally less than 100 mm.

In this embodiment the illumination chamber 7 has a height H between the lower and upper surfaces 23, 25, here of 45 mm.

In one embodiment the height H is less than 150 mm, optionally less than 120 mm, and optionally less than 100 mm.

In this embodiment the light source 11 is disposed at or adjacent the rear surface 21 of the housing 6, extending therealong.

In this embodiment the lower and upper surfaces 23, 25 have a diffuse finish, and the housing 6 provides an integrating box.

In an alternative embodiment the lower and upper surfaces 23, 25 could have a specular finish, and the housing 6 provides a mirror box.

In this embodiment the lower and upper surfaces 23, 25 are disposed in substantially parallel relation.

In this embodiment at least one of the lower and upper surfaces 23, 25 has a first region 40, and at least one second region 41 which has a different optical property to an optical property of the first region 40.

The present inventors have recognized that, by altering the optical properties of at least one of the lower and upper surfaces 23, 25 of the illumination chamber 7, the profile of the delivered illumination can be controlled, both to accommodate variance in the light generated by the light source 11 and also to accommodate variance in the light profile of the at least one associated foreground illumination devices 5a-d, such that a substantially-uniform light profile can be presented at the field of view, here at the chute 2.

In this embodiment at least one of the lower and upper surfaces 23, 25 has a plurality of second regions 41 of different optical properties to the optical properties of the first region 40.

In this embodiment at least one of the lower and upper surfaces 23, 25 has a pair of second regions 41 of different optical properties to the optical properties of the first region 40, which are located to respective ones of rear and outward lateral sections of the at least one of the lower and upper surfaces 23, 25, adjacent the light source 11.

In this embodiment the second regions 41 are spaced from one another by a distance d, here by a distance of 250 mm.

In this embodiment the second regions 41 each have a length l, here of 775 mm.

In this embodiment the length l is less than half of the length L of the illumination chamber 7.

In this embodiment the second regions 41 are triangular is shape, and have a projection p, here of 18 mm, at the outer lateral edges of the illumination chamber 7, tapering inwardly to a central region of the illumination chamber 7.

In an alternative embodiment the second regions 41 could be regions of varying radial dimension, such as circles of varying diameter, so as to create a more complex stippled pattern.

In this embodiment the projection p has a length of less than half of the depth D of the illumination chamber 7, optionally less than one-third of the illumination chamber 7, and optionally less than one-quarter of the illumination chamber 7.

In this embodiment the first and second regions 40, 41 have a different color and/or a different surface color and/or a different spectral reflectance, with the first region being made of or coated with a high-diffuse reflectance material, such as white paint and the at least one second region 41 being made of or coated with low reflectance material or coating, such as black paint. It will, however, be understood that the first and second regions 40, 41 could have any different colors or surface colors or spectral reflectances.

In another embodiment the first and second regions 40, 41 could have a different surface texture with a different scattering fraction and distribution.

In one embodiment the first and second regions 40, 41 could have a different color and/or different surface color and/or different spectral reflectance and/or different texture.

In this embodiment each of the lower and upper surfaces 23, 25 has at least one second region 41 of different optical properties.

In this embodiment the light source 11 is an elongate light-emitting diode (LED) light source which comprises a plurality of LEDs 51 spaced along a length thereof.

In this embodiment ones of the LEDs have different spectral output or color, so as to allow for control of the spectral output or color.

In one embodiment selected ones or groups of ones of the LEDs 51 can be controlled independently so as to control the pitch and/or intensity of the LEDs 51, such as by varying the drive current.

Figure 4A:
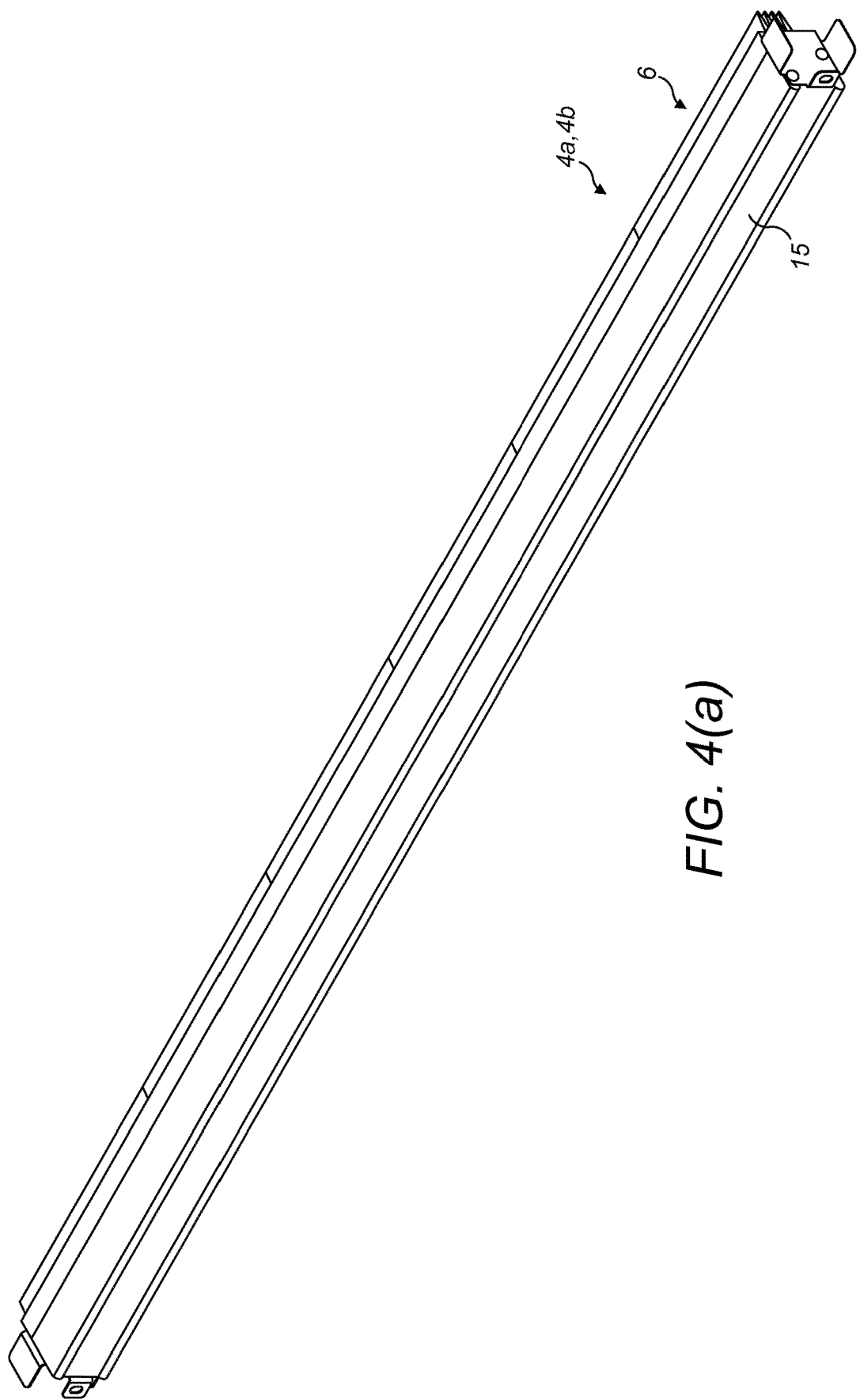
FIG. 4(a) illustrates a perspective view of a background illumination device in accordance with another embodiment of the present invention.
Figure 4B:
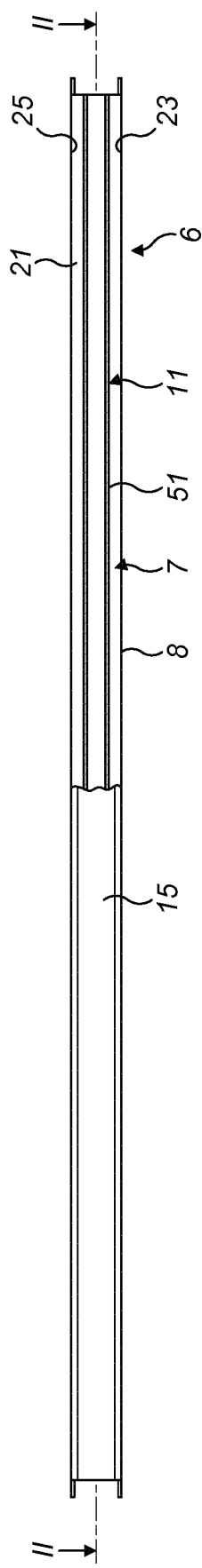
FIG. 4(b) illustrates a part cut-away front view of the illumination device of FIG. 4(a)
Figure 4C:
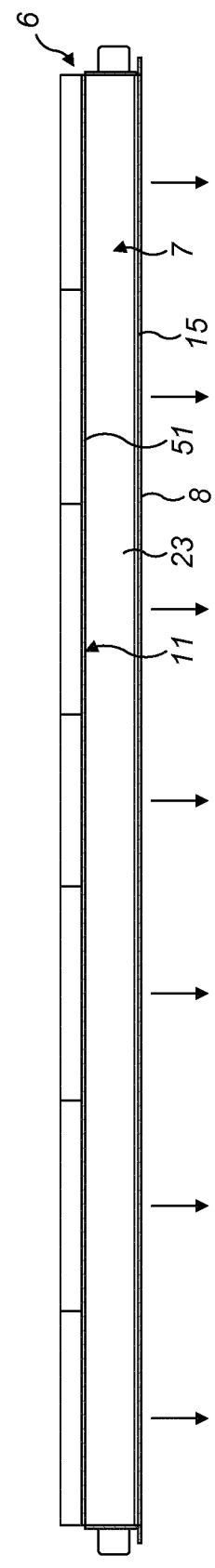
FIG. 4(c) illustrates a longitudinal sectional view (along section II-II in FIG. 4(b)) of the illumination device of FIG. 4(a)

FIGS. 4(a) to (c) illustrate a background illumination device 4a, b, for providing background illumination to the at least one detector 3a, b, in accordance with another embodiment of the present invention.

The illumination device comprises a housing 6 which includes an elongate illumination chamber 7, which has an elongate illumination aperture 8, a light source 11 which extends along a length of the illumination chamber 7, and a light diffuser 15 which is disposed at the illumination aperture 8 and diffuses the light thereat.

In this embodiment the illumination chamber 7 comprises a first, rear surface 21, second and third, lower and upper surfaces 23, 25 which are disposed in spaced relation and extend forwardly from the rear surface 21 to the illumination aperture 8, and fourth and fifth, side surfaces 27, 29, which define the lateral ends of the illumination chamber 7 and extend forwardly from the rear surface 21 to the illumination aperture 8.

In this embodiment the illumination chamber 7 has a length L, here of 1800 mm.

In this embodiment the illumination chamber 7 has a depth D between the light source 11 and the diffuser 15, here of 70 mm.

In one embodiment the depth D is less than 200 mm, optionally less than 150 mm, and optionally less than 100 mm.

In this embodiment the illumination chamber 7 has a height H between the lower and upper surfaces 23, 25, here of 45 mm.

In one embodiment the height H is less than 150 mm, optionally less than 120 mm, and optionally less than 100 mm.

In this embodiment the light source 11 is disposed at or adjacent the rear surface 21 of the housing 6, extending therealong.

In this embodiment the lower and upper surfaces 23, 25 have a diffuse finish, and the housing 6 provides an integrating box.

In an alternative embodiment the lower and upper surfaces 23, 25 could have a specular finish, and the housing 6 provides a mirror box.

In this embodiment the lower and upper surfaces 23, 25 are disposed in substantially parallel relation.

In this embodiment the lower and upper surfaces 23, 25 comprise a specular reflectance material or coating or a diffuse reflectance material or coating, such as white paint. Lower and upper surfaces 23, 25 may also comprise a material or coating that has any ratio of specular to diffuse reflectance.

In one alternative embodiment the lower and upper surfaces 23, 25 could have a color other than white or a reflectance that varies with wavelength.

In one embodiment the lower and upper surfaces 23, 25 have optical properties which are matched to the light source 11, which may involve use of materials, coatings or surface finishes with spectral reflectance, low or high, matched to the light source 11.

In this embodiment the rear and side surfaces 21, 27, 29 comprise a specular reflectance material or coating, a diffuse reflectance material or coating, such as white paint, or low reflectance material or coating, such as black paint. Rear and side surfaces 21, 27, 29 may also comprise a material or coating that has any ratio of specular to diffuse reflectance.

In one alternative embodiment the rear and side surfaces 21, 27, 29 could have a color other than white or black or have a reflectance that varies with wavelength or have a low reflectance.

In one embodiment the lower and upper surfaces 23, 25 could have different optical properties to the rear and side surfaces 21, 27, 29.

In this embodiment the light source 11 is an infra-red (IR) light-emitting diode (LED) light source with an emission spectrum within the near infra-red (NIR) and/or short-wave infra-red (SWIR) regions, encompassing wavelengths from about 700 nm to about 2.5 μm.

The present inventors have recognized that the application of such an IR LED light source in an illumination box, which has controlled spectral reflectance, advantageously provides background illumination which allows for the discrimination of dark foreign matter from dark (acceptable) product.

In this embodiment the light source comprises a plurality of LEDs 51 which are spaced along a length of the illumination chamber 7.

In one embodiment selected ones or groups of ones of the LEDs 51 can be controlled independently so as to control the pitch and/or intensity of the LEDs 51, such as by varying the drive current.

Figure 5A:
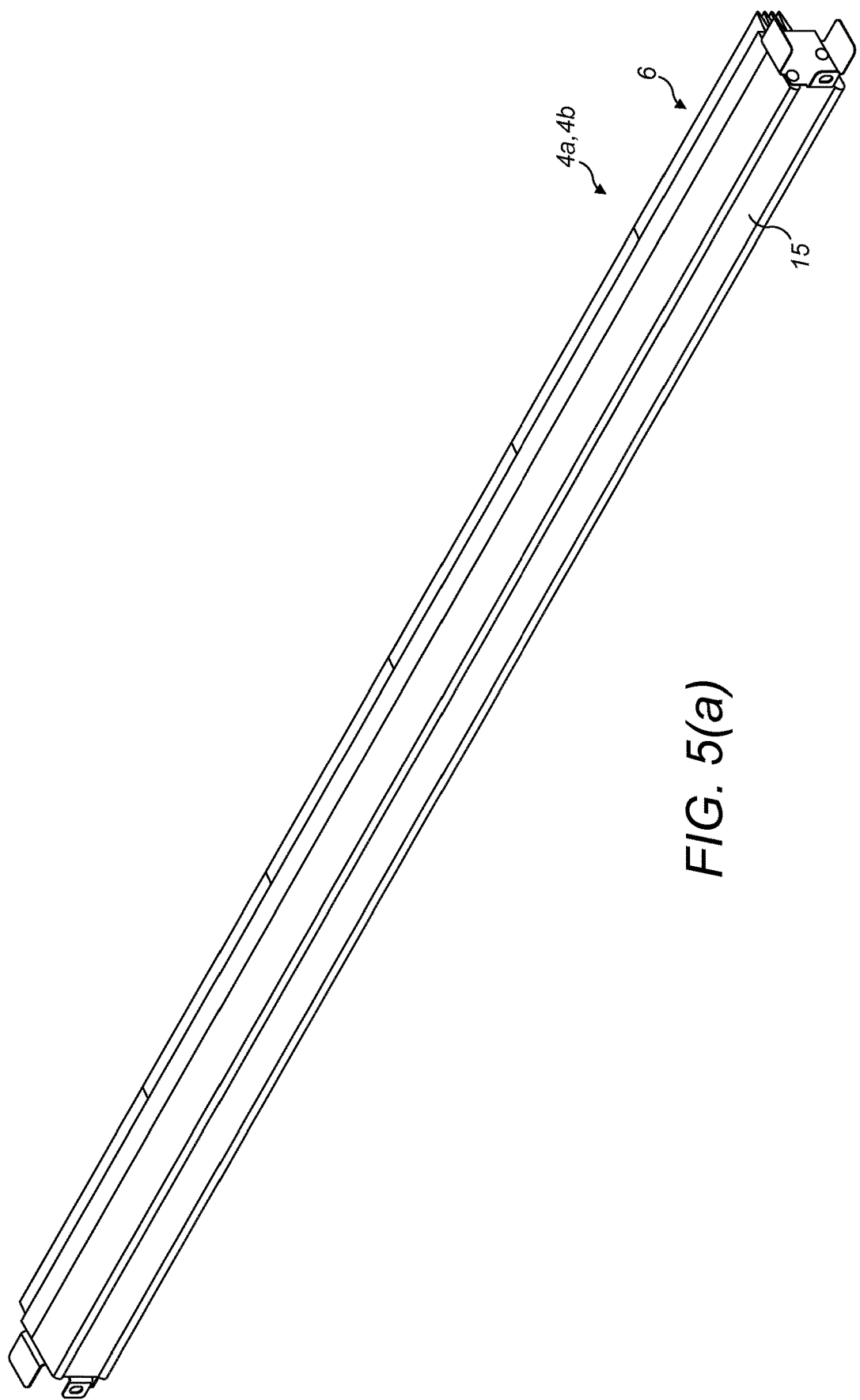
FIG. 5(a) illustrates a perspective view of a background illumination device in accordance with a further embodiment of the present invention.
Figure 5B:
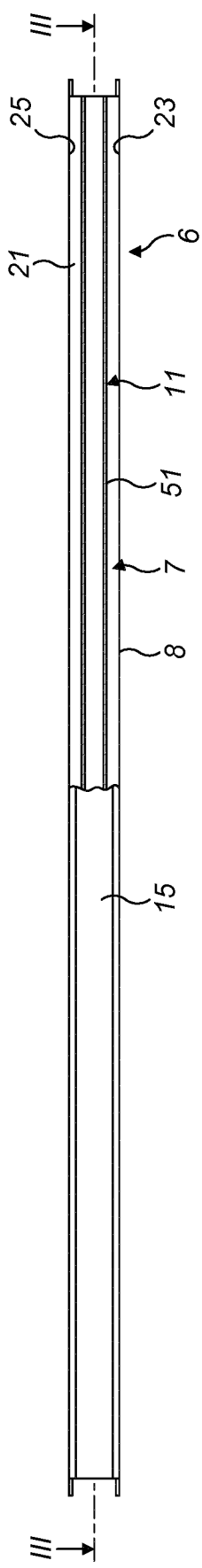
FIG. 5(b) illustrates a part cut-away front view of the illumination device of FIG. 5(a)
Figure 5C:
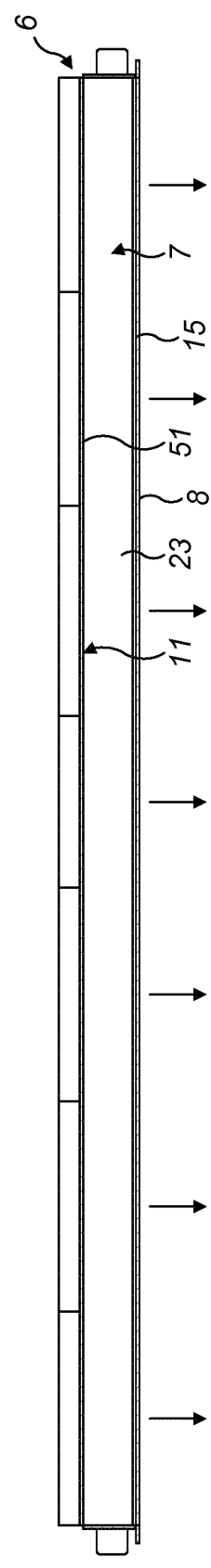
FIG. 5(c) illustrates a longitudinal sectional view (along section in FIG. 5(b)) of the illumination device of FIG. 5(a)
Figure 5D:
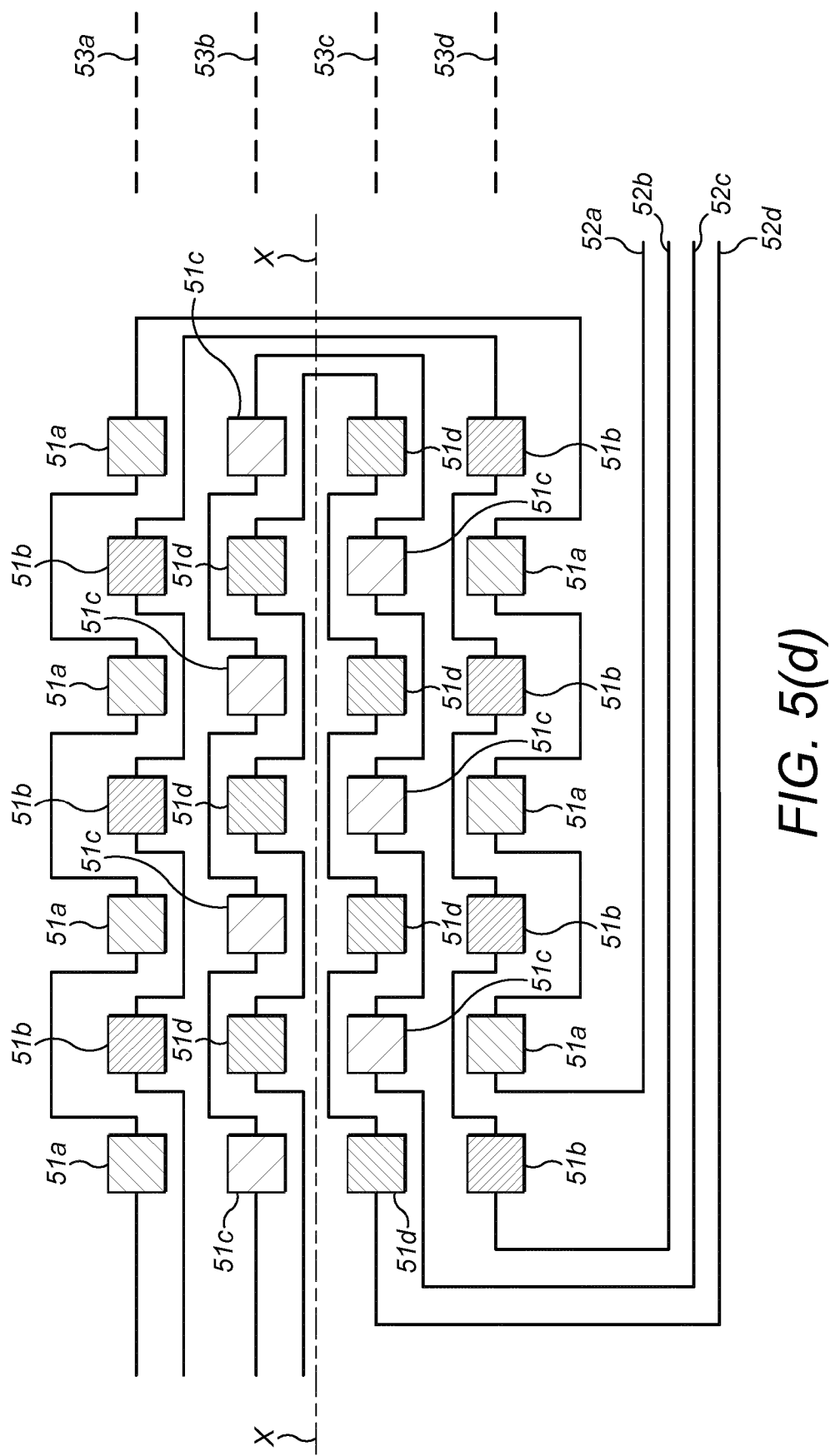
FIG. 5(d) illustrates a fragmentary view of the light source of the illumination device of FIG. 5(a)

FIGS. 5(a) to (c) illustrate a background illumination device 4a, b, for providing background illumination to the at least one detector 3a, b, in accordance with a further embodiment of the present invention.

The illumination device comprises a housing 6 which includes an elongate illumination chamber 7, which has an elongate illumination aperture 8, a light source 11 which extends along a length of the illumination chamber 7, and a light diffuser 15 which is disposed at the illumination aperture 8 and diffuses the light thereat.

In this embodiment the illumination chamber 7 comprises a first, rear surface 21, second and third, lower and upper surfaces 23, 25 which are disposed in spaced relation and extend forwardly from the rear surface 21 to the illumination aperture 8, and fourth and fifth, side surfaces 27, 29, which define the lateral ends of the illumination chamber 7 and extend forwardly from the rear surface 21 to the illumination aperture 8.

In this embodiment the illumination chamber 7 has a length L, here of 1800 mm.

In this embodiment the illumination chamber 7 has a depth D between the light source 11 and the diffuser 15, here of 70 mm.

In one embodiment the depth D is less than 200 mm, optionally less than 150 mm, and optionally less than 100 mm.

In this embodiment the illumination chamber 7 has a height H between the lower and upper surfaces 23, 25, here of 45 mm.

In one embodiment the height H is less than 150 mm, optionally less than 120 mm, and optionally less than 100 mm.

In this embodiment the light source 11 is disposed at or adjacent the rear surface 21 of the housing 6, extending therealong.

In this embodiment the lower and upper surfaces 23, 25 have a diffuse finish, and the housing 6 provides an integrating box.

In an alternative embodiment the lower and upper surfaces 23, 25 could have a specular finish, and the housing 6 provides a mirror box.

In this embodiment the lower and upper surfaces 23, 25 are disposed in substantially parallel relation.

In this embodiment the lower and upper surfaces 23, 25 comprise a specular reflectance material or coating or are made of or coated with a diffuse reflectance material, such as white paint. Lower and upper surfaces 23, 25 may also comprise a material or coating that has any ratio of specular to diffuse reflectance.

In one alternative embodiment the lower and upper surfaces 23, 25 could have a color other than white or a reflectance that varies with wavelength.

In this embodiment the rear and side surfaces 21, 27, 29 comprise a specular reflectance material or coating or are made of or coated with a diffuse reflectance material, such as white paint or are made of or coated with low reflectance material or coating, such as black paint.

In one alternative embodiment the rear and side surfaces 21, 27, 29 could have a color other than white or black.

In one embodiment the lower and upper surfaces 23, 25 could have a different surface texture to the rear and side surfaces 21, 27, 29.

In this embodiment the light source 11 is a light-emitting diode (LED) light source which comprises a plurality of LEDs 51 which are spaced along a length of the illumination chamber 7.

In this embodiment the LEDs 51 comprise LEDs 51a-d of a plurality of different wavelengths or colors.

In this embodiment the LEDs 51a-d have four different wavelengths or colors, but could have any number of two or greater.

In this embodiment the LEDs 51a-d are blue, green, red and far-red in color.

In this embodiment the LEDs 51a-d of each wavelength or color are connected to a common channel 52a-d, such that the LEDs 51a-d of one wavelength or color are switchable independently of the LEDs 51a-d of the other wavelengths or colors.

In this embodiment the LEDs 51a-d are arranged on a plurality of rows 53a-d which extend along a length of the illumination chamber 7.

In this embodiment the LEDs 51a-d are arranged on four rows 53a-d, but could have any number of two or greater.

In this embodiment the LEDs 51a-d are arranged in substantially symmetrical relation about the longitudinal axis of the light source 11.

In this embodiment the LEDs 51a-d of each wavelength or color are arranged on a plurality of different rows 53a-d which have symmetrical relation about the longitudinal axis of the light source 11, such that a substantially an equal number of LEDs 51a-d of each wavelength or color are arranged along the length of the light source 11.

The present inventors have recognized an arrangement of the LEDs 51a-d of different wavelength or color which provides multi-wavelength or multi-color background illumination with a symmetrical profile, and yet allows for separation of the LEDs 51a-d, which enables distribution of the thermal load and also allows for the accommodation of other components between ones of the rows 53a-d. Furthermore, this arrangement of the LEDs 51a-d allows for independent switching.

FIGS. 6(a) to (g) illustrate a foreground illumination device 5a-d, for providing foreground illumination to the at least one detector 3a, b, in accordance with one embodiment of the present invention.

The illumination device comprises a reflector 61 which provides a reflector surface 63, and a lighting assembly 64 which is disposed in front of the reflector surface 63 and provides light of a first wavelength to the reflector surface 63 for reflection thereby to a field of view of the at least one detector 3a, b.

In this embodiment the reflector 61 is an elongate, linear reflector.

In this embodiment the reflector 61 comprises a support 66 and a reflector element 67 which provides the reflector surface 63 and is attached to the support 66.

In this embodiment the reflector element 67 is attached to the support 66 by folded tabs 68.

In this embodiment the reflecting surface 63 is an elliptical surface. The reflector surface 63 may be made, for instance, from a material or coating that has high specular reflectance or from a material that has high-diffuse reflectance or from a material that has any scattering fraction and distribution.

In this embodiment the lighting assembly 64 a first light source 70 which is disposed in front of the reflecting surface 63 and provides light of a first wavelength to the reflecting surface 63 of the reflector 61, and a second light source 71 of a second wavelength, different to the first wavelength, which is disposed in front of the reflecting surface 63 and provides light of a first wavelength to the reflecting surface 63 of the reflector 61.

Figure 6A:
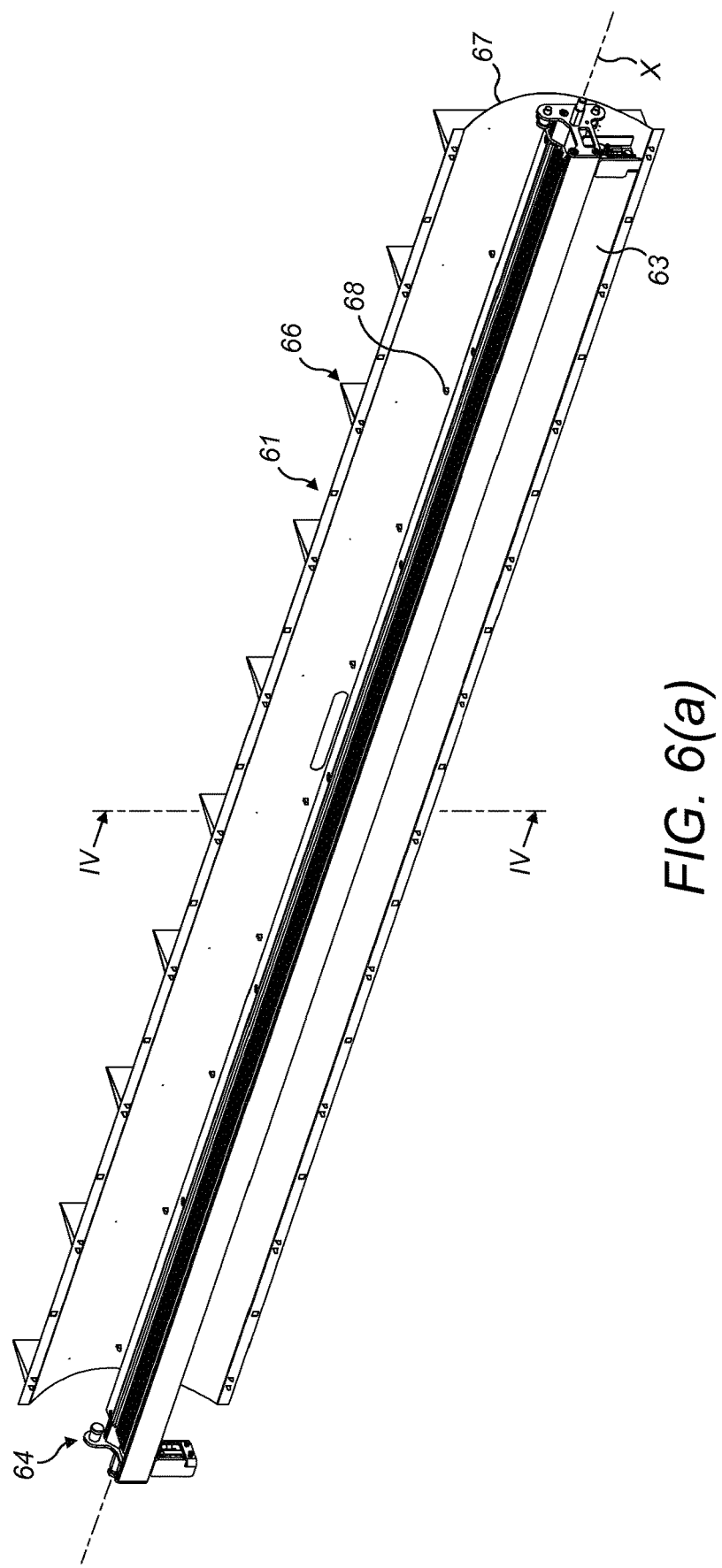
FIG. 6(a) illustrates a perspective view of a foreground illumination device in accordance with one embodiment of the present invention.
Figure 6B:
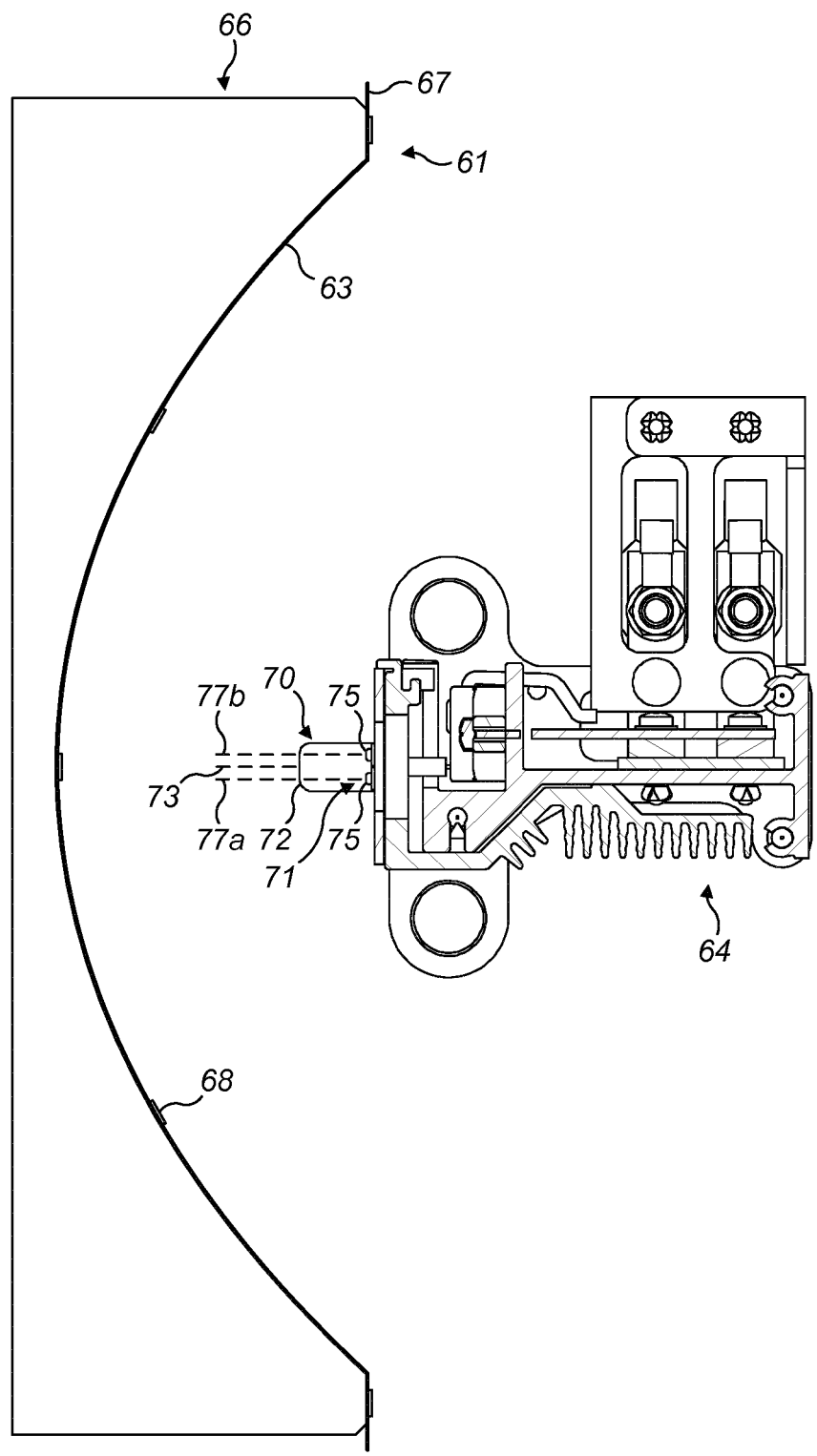
FIG. 6(b) illustrates a vertical sectional view (along section IV-IV in FIG. 6(a)) of the illumination device of FIG. 6(a)
Figure 6C:
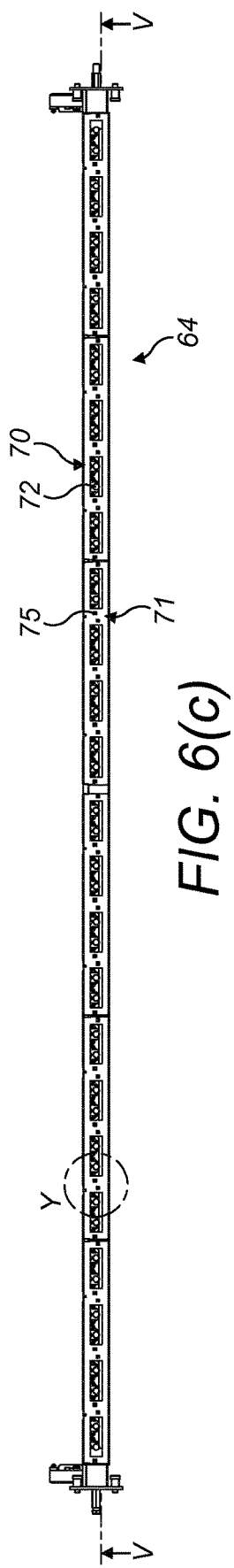
FIG. 6(c) illustrates a front view of the light assembly of the illumination device of FIG. 6(a)
Figure 6D:
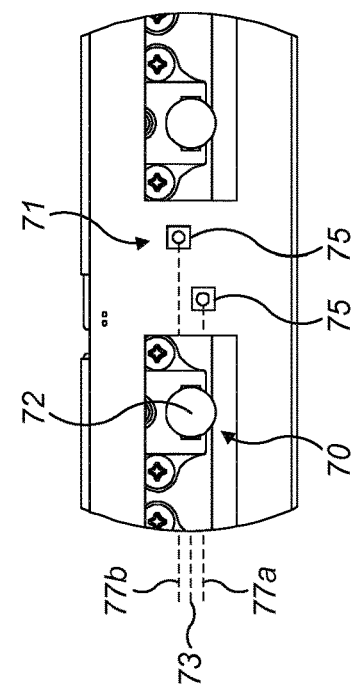
FIG. 6(d) illustrates in enlarged scale a fragmentary front view (detail Y in FIG. 6(c)) of the light assembly of FIG. 6(c)
Figure 6G:
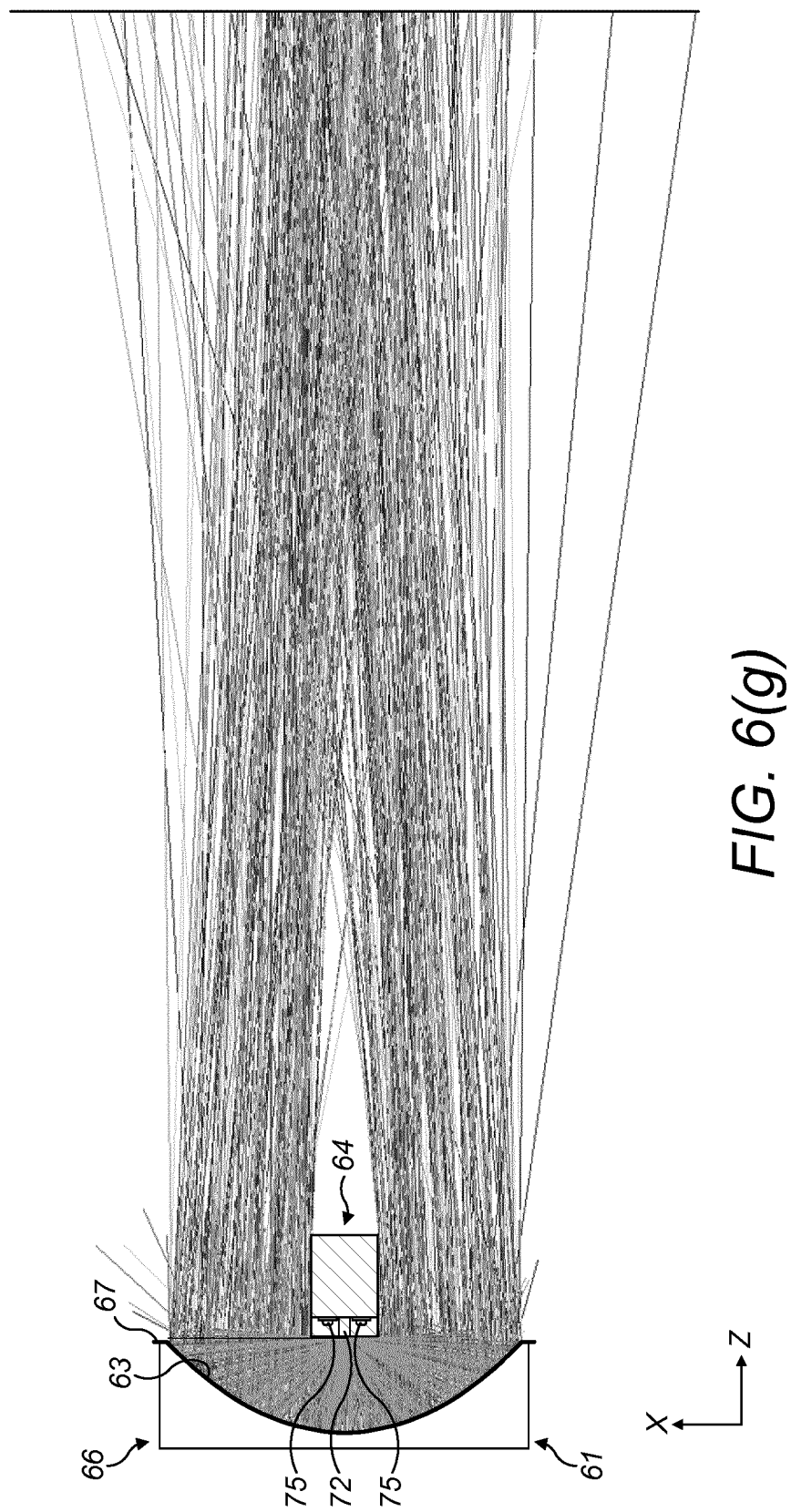
FIG. 6(g) illustrates a ray diagram for the light profile as developed by the illumination device of FIG. 6(a).

In this embodiment the first and second light sources 70, 71 are disposed within and in symmetrical relation to the reflector 61, and so provide illumination of different wavelength which is co-incident at the field of view of the at least one detector 3a, b, as represented in FIG. 6(g).

In this embodiment the first light source 70 is an incandescent light source emitting blackbody or greybody radiation with an emission spectrum within the visible, near infra-red (NIR) and/or short-wave infra-red (SWIR) regions.

In this embodiment the first light source 70 provides light with a wavelength of from about 400 nm to about 2.5 μm, but light of other wavelengths can be provided in other embodiments.

In this embodiment the first light source 70 is an incandescent light source.

In alternative embodiments the first light source 70 could comprise light-emitting diodes (LEDs), near infra-red (NIR) light-emitting diodes (LEDs) or lasers, such as vertical-cavity surface-emitting lasers (VCSELs).

In this embodiment the first light source 70 comprises a plurality of incandescent lamps 72.

In this embodiment the lamps 72 are arranged along a single row 73.

In this embodiment the lamps 72 are disposed on or near a focal axis X (sometimes referred to as the optical axis or longitudinal axis) of the reflector 61.

In this embodiment the lamps 72 comprise Xenon incandescent lamps, but could be other incandescent lamps, such as halogen lamps.

In this embodiment the lamps 72 comprise axial filament lamps, but could be transverse filament lamps or festoons.

In this embodiment the second light source 71 is a visible light source.

In this embodiment the second light source 71 provides light with a wavelength of from about 400 nm to about 780 nm.

In this embodiment the second light source 71 is a light-emitting diode (LED) light source.

In alternative embodiments the first light source 70 could comprise incandescent lamps, near infra-red (NIR) light-emitting diodes (LEDs) or lasers, such as vertical-cavity surface-emitting lasers (VCSELs).

In this embodiment the second light source 71 comprises a plurality of LEDs 75.

In this embodiment the LEDs 75 are disposed on or near a focal axis X (sometimes referred to as the optical axis or longitudinal axis) of the reflector 61.

In this embodiment the LEDs 75 are arranged along a plurality of rows 77a, b, which each extend along the length of the reflecting surface 63 and are arranged in spaced relation in a direction substantially parallel to the focal axis X of the reflector 61.

In this embodiment the rows 77a, b are spaced in symmetrical relation to the focal axis X of the reflector 61.

In this embodiment the LEDs 75 in the rows 77a, b are offset in staggered relation along the length of the second light source 71.

The present inventors have recognized that, by providing the LEDs 75 in spaced, staggered rows 77a, b, the irradiance profiles of the LEDs 75 and the incandescent lamps 72 can be more closely matched.

Finally, it will be understood that the present invention has been described in its preferred embodiments and can be modified in many different ways without departing from the scope of the invention as defined by the appended claims.

Various further aspects of the invention are identified in the numbered paragraphs below.

1. An illumination device which provides illumination or foreground illumination in a sorting or classifying apparatus, the illumination device comprising a reflector (61) which has a reflecting surface (63) providing a reflection envelope, a first light source (70) which is disposed in spaced relation in front of the reflecting surface (63) and provides light of a first spectral output to the reflecting surface (63) for reflection thereby, and a second light source (71) which is disposed in spaced relation in front of the reflecting surface (63) and provides light of a second spectral output, different to the first spectral output to the reflecting surface (63) for reflection thereby, optionally the first light source (70) is a source of near infra-red (NIR) light and the second light source (71) is a source of visible-spectrum light.
2. The illumination device of paragraph 1, wherein:
  (i) the reflector (61) is an elongate, linear reflector, and optionally the reflecting surface (63) is an elliptical surface;
  (ii) the first and second light sources (70, 71) are disposed within the reflection envelope of the reflector (61) and in symmetrical relation to the reflector (61), thereby providing co-incident illumination of different wavelengths; and/or
  (iii) the first light source (70), optionally an incandescent light source, provides light with a wavelength of from about 400 nm to about 2.5 µm, and the second light source (71), optionally a light-emitting diode (LED) light source, provides light with a wavelength of from about 400 nm to about 780 nm.
3. The illumination device of paragraph 1 or 2, wherein the first light source (70) comprises a plurality of light elements or incandescent lamps (72), optionally arranged along a single row (73), optionally the light elements or lamps (72) are disposed on or near a focal plane of the reflector (61).
4. The illumination device of any of paragraphs 1 to 3, wherein the second light source (71) comprises a plurality of light elements or light-emitting diodes (LEDs) (75), optionally arranged along a plurality of rows (77a, b) which each extend along the length of the reflecting surface (63) and are arranged in spaced relation in a direction substantially parallel to the optical axis of the reflector (61), optionally the rows (77a, b) are arranged in symmetrical spaced relation to the optical axis of the reflector (61), optionally the light elements or light-emitting diodes (LEDs) (75) in the rows (77a, b) are offset in staggered relation along the length of the second light source (71).
5. An illumination device for providing illumination or background or reference illumination in a sorting or classifying apparatus, the illumination device comprising a housing (6) which includes an elongate illumination chamber (7) having an illumination aperture (8), the illumination chamber (7) comprising a first, rear surface (21) and second and third, lower and upper surfaces (23, 25) which are disposed in spaced relation and extend forwardly from the rear surface (21) to the illumination aperture (8), and a light source (11) which extends along a length of the illumination chamber (7), wherein at least one of the lower and upper surfaces (23, 25), optionally both the lower and upper surfaces (23, 25), has a first region (40) and at least one second region (41) which has different optical properties to optical properties of the first region (40).
6. The illumination device of paragraph 5, wherein:
  (i) the light source (11) is an infra-red (IR) light-emitting diode (LED) light source with an emission spectrum within the near infra-red (NIR) and/or short-wave infra-red (SWIR) regions, encompassing wavelengths from about 700 nm to about 2.5 µm;
  (ii) the light source (11) has an emission spectrum encompassing wavelengths from about 700 nm to about 2.5 µm; and/or
  (iii) the light source (11) is disposed at or adjacent the rear surface (21), extending therealong.
7. The illumination device of paragraph 5 or 6, wherein:
  (i) the illumination chamber (7) has a depth (D) between the light source (11) and the illumination aperture (8) of less than 200 mm, preferably less than 150 mm, and most preferably less than 100 mm;
  (ii) the illumination chamber (7) has a height (H) between the lower and upper surfaces (23, 25) of less than 150 mm, preferably less than 120 mm, and most preferably less than 100 mm;
  (iii) the lower and upper surfaces (23, 25) are disposed in substantially parallel relation;
  (iv) the lower and upper surfaces (23, 25) have a diffuse finish and the housing (6) provides an integrating box, or the lower and upper surfaces (23, 25) have a specular finish and the housing (6) provides a mirror box;
  (v) the lower and upper surfaces (23, 25) comprise a specular reflectance material or coating or a diffuse reflectance material or coating, optionally painted with white paint; and/or
  (vi) at least one of the lower and upper surfaces (23, 25) has a plurality of second regions (41) of different optical properties to the optical properties of the first region (40).
8. The illumination device of any of paragraphs 5 to 7, wherein at least one of the lower and upper surfaces (23, 25) has a plurality of second regions (41) of different optical properties to the optical properties of the first region (40), optionally;
  (i) at least one of the lower and upper surfaces (23, 25) has a pair of second regions (41) of different optical properties to the optical properties of the first region (40), which are located to respective ones of rear and outward lateral sections of the at least one of the lower and upper surfaces (23, 25), adjacent the light source (11);
  (ii) the second regions (41) are spaced from one another by a distance (d);
  (iii) the second regions (41) each have a length (l) which is less than half of the length (L) of the illumination chamber (7); and/or
  (iv) the second regions (41) are substantially triangular in shape, and have a projection (p) at the outer lateral edges of the illumination chamber (7), tapering inwardly to a central region of the illumination chamber (7), optionally the projection (p) has a length of less than half of the depth (D) of the illumination chamber (7), preferably less than one-third of the depth (D) of the illumination chamber (7), and most preferably less than one-quarter of the depth (D) of the illumination chamber (7).
9. The illumination device of any of paragraphs 5 to 8, wherein:
  (i) the first and second regions (40, 41) have a different surface color and/or a different spectral reflectance, optionally the first region (40) being made of or coated with a diffuse reflectance material, such as optionally white paint and the at least one second region (41) being made of or coated with low reflectance material, such as optionally black paint; and/or
  (ii) the first and second regions (40, 41) have different optical properties.
10. The illumination device of any of paragraphs 5 to 9, wherein:
  (i) the rear surface (21) comprises a specular reflectance material or coating or a diffuse reflectance material or coating, optionally painted with white paint, or a low reflectance material or coating, such as optionally painted with black paint; and/or (ii) the rear surface (21) has different optical properties to the lower and upper surfaces (23, 25).
11. The illumination device of any of paragraphs 5 to 10, wherein the illumination chamber (7) further comprises fourth and fifth, side surfaces (27, 29) which define the lateral ends of the illumination chamber (7), optionally:
   (i) the side surfaces (27, 29) comprise a specular reflectance material or coating or a diffuse reflectance material or coating, optionally painted with white paint, or a low reflectance material or coating, such as optionally painted with black paint; and/or
   (ii) the side surfaces (27, 29) have different optical properties to the lower and upper surfaces (23, 25).
12. The illumination device of any of paragraphs 5 to 11, wherein the light source (11) is an elongate light-emitting diode (LED) light source which comprises a plurality of light-emitting diodes (LEDs) (51) spaced along a length thereof, optionally ones or groups of ones of the LEDs (51) are of different wavelengths or colors, optionally selected ones or groups of ones of the LEDs (51) can be controlled independently so as to control the pitch and/or intensity of the LEDs (51).
13. An illumination device for providing illumination or background or reference illumination in a sorting or classifying apparatus, the illumination device comprising an elongate light source (11) which comprises an array of LEDs (51a-d) of a plurality of different wavelengths or colors, wherein the LEDs (51a-d) are arranged in substantially symmetrical relation to opposite sides of a longitudinal axis of the light source (11).
14. The illumination device of paragraph 13, wherein:
   (i) the LEDs (51a-d) are of three or more different wavelengths or colors;
   (ii) the LEDs (51a-d) of each wavelength or color are connected to a common channel (52a-d), such that the LEDs (51a-d) of one wavelength or color are switchable independently of the LEDs (51a-d) of other wavelengths or colors; and/or
   (iii) the LEDs (51a-d) are arranged in a plurality of rows (53a-d) which extend in substantially parallel relation to the longitudinal axis of the light source (11), optionally the LEDs (51a-d) are arranged in three or more rows (53a-d).
15. An illumination device for providing illumination or background or reference illumination in a sorting or classifying apparatus, the illumination device comprising a housing (6) which includes an elongate illumination chamber (7) having an illumination aperture (8), the illumination chamber (7) comprising a first, rear surface (21) and second and third, lower and upper surfaces (23, 25) which are disposed in spaced relation and extend forwardly from the rear surface (21) to the illumination aperture (8), and a light source (11) which extends along a length of the illumination chamber (7), the light source (11) being an infra-red (IR) light-emitting diode (LED) light source, optionally having an emission spectrum within the near infra-red (NIR) and/or short-wave infra-red (SWIR) regions.

The invention claimed is:
1. A sorting or classifying apparatus comprising a foreground illumination device for providing foreground illumination, the foreground illumination device comprising
   a reflector which has a reflecting surface providing a reflection envelope,
   a first light source which is disposed in spaced relation in front of and faces the reflecting surface and provides light of a first spectral output to the reflecting surface for reflection thereby, the first light source comprising a plurality of incandescent lamps which are disposed on or near a focal axis of the reflector, and
   a second light source which is disposed in spaced relation in front of and faces the reflecting surface and provides light of a second spectral output, different to the first spectral output to the reflecting surface for reflection thereby, the second light source comprising a plurality of light elements arranged along at least one row which extends along the length of the reflecting surface and is arranged in a direction substantially parallel to the focal axis of the reflector.
2. The sorting or classifying apparatus of claim 1, wherein:
   (i) the reflector is an elongate, linear reflector;
   (ii) the first and second light sources are disposed within the reflection envelope of the reflector and in symmetrical relation to the reflector, thereby providing co-incident illumination of different wavelengths; and/or
   (iii) the first light source provides light with a wavelength of from about 400 nm to about 2.5 µm, and the second light source provides light with a wavelength of from about 400 nm to about 780 nm.
3. The sorting or classifying apparatus of claim 1, wherein the incandescent lamps are arranged along a single row.
4. The sorting or classifying apparatus of claim 1, wherein the at least one row includes a plurality of rows of light elements arranged in symmetrical spaced relation to the focal axis (X) of the reflector, with the light elements in the rows being offset in staggered relation along the length of the second light source.
5. A sorting or classifying apparatus comprising
   a foreground illumination device for providing foreground illumination and
   an illumination box for providing background or reference illumination,
   the illumination box comprising a housing which includes an elongate illumination chamber having an illumination aperture,
   the illumination chamber comprising a first, rear surface and second and third, lower and upper surfaces which are disposed in spaced relation and extend forwardly from the rear surface to the illumination aperture and are disposed in substantially parallel relation,
   a light diffuser which is disposed at the illumination aperture and a light source which extends along a length of the illumination chamber,
   wherein at least one of the lower and upper surfaces has a first region and at least one second region which has different optical properties to optical properties of the first region such that the illumination box accommodates for variance in light generated by the light source and also for variance in light generated by the illumination device.
6. A sorting or classifying apparatus according to claim 1 and further comprising a background or reference illumination device for providing background or reference illumination, the background or reference illumination device comprising a diffuser and an elongate light source which comprises a two-dimensional array of separated LEDs of a plurality of different wavelengths or colors, wherein the LEDs are arranged in substantially symmetrical relation to opposite sides of a longitudinal axis of the light source of the background or reference illumination device and the LEDs of each wavelength or color are connected to a common channel, such that the LEDs of one wavelength or color are switchable independently of the LEDs of other wavelengths or colors, such that a symmetrical illumination profile is provided.

7. The sorting or classifying apparatus of claim 6, wherein:
   (i) the LEDs are of three or more different wavelengths or colors; and/or
   (ii) the LEDs are arranged in a plurality of rows which extend in substantially parallel relation to the longitudinal axis of the light source of the background or reference illumination device.

8. A sorting or classifying apparatus according to claim 1, further comprising an illumination box for providing background or reference illumination, the illumination box comprising a housing which includes an elongate illumination chamber having an illumination aperture, the illumination chamber comprising a first, rear surface and second and third, lower and upper surfaces which are disposed in spaced relation and extend forwardly from the rear surface to the illumination aperture and are disposed in substantially parallel relation, and a light source which extends along a length of the illumination chamber, the light source of the illumination box being an infra-red (IR) light-emitting diode (LED) light source.

9. The sorting or classifying apparatus of claim 1, wherein the first light source is a source of near infra-red (NIR) light and the second light source is a source of visible-spectrum light.

10. The sorting or classifying apparatus of claim 5, wherein:
   (i) the light source is an infra-red (IR) light-emitting diode (LED) light source with an emission spectrum within the near infra-red (NIR) and/or short-wave infra-red (SWIR) regions, encompassing wavelengths from about 700 nm to about 2.5 µm;
   (ii) the light source has an emission spectrum encompassing wavelengths from about 700 nm to about 2.5 µm; and/or
   (iii) the light source is disposed at or adjacent the rear surface, extending therealong.

11. The sorting or classifying apparatus of claim 5, wherein:
   (i) the illumination chamber has a depth between the light source and the illumination aperture of less than 200 mm;
   (ii) the illumination chamber has a height between the lower and upper surfaces of less than 150 mm;
   (iii) the lower and upper surfaces have a diffuse finish and the housing provides an integrating box, or the lower and upper surfaces have a specular finish and the housing provides a mirror box;
   (iv) the lower and upper surfaces comprise a specular reflectance material or coating or a diffuse reflectance material or coating; and/or
   (v) at least one of the lower and upper surfaces has a plurality of second regions of different optical properties to the optical properties of the first region.

12. The sorting or classifying apparatus of claim 5, wherein at least one of the lower and upper surfaces has a plurality of second regions of different optical properties to the optical properties of the first region,
   (i) at least one of the lower and upper surfaces has a pair of second regions of different optical properties to the optical properties of the first region, which are located to respective ones of rear and outward lateral sections of the at least one of the lower and upper surfaces, adjacent the light source;
   (ii) the second regions are spaced from one another by a distance;
   (iii) the second regions each have a length which is less than half of the length of the illumination chamber; and/or
   (iv) the second regions are substantially triangular in shape, and have a projection at the outer lateral edges of the illumination chamber, tapering inwardly to a central region of the illumination chamber.

13. The sorting or classifying apparatus of claim 5, wherein:
   (i) the first and second regions have a different surface color and/or a different spectral reflectance; and/or
   (ii) the first and second regions have different optical properties.

14. The sorting or classifying apparatus of claim 5, wherein:
   (i) the rear surface comprises a specular reflectance material or coating or a diffuse reflectance material or coating; and/or
   (ii) the rear surface has different optical properties to the lower and upper surfaces.

15. The sorting or classifying apparatus of claim 5, wherein the illumination chamber further comprises fourth and fifth, side surfaces which define the lateral ends of the illumination chamber,
   (i) the side surfaces comprise a specular reflectance material or coating or a diffuse reflectance material or coating; and/or
   (ii) the side surfaces have different optical properties to the lower and upper surfaces.

16. The sorting or classifying apparatus of claim 5, wherein the light source is an elongate light-emitting diode (LED) light source which comprises a plurality of light-emitting diodes (LEDs) spaced along a length thereof.

* * * * *

UNITED STATES PATENT AND TRADEMARK OFFICE
CERTIFICATE OF CORRECTION

PATENT NO. : 10,987,701 B2
APPLICATION NO. : 16/313675
DATED : April 27, 2021
INVENTOR(S) : David Gherardi et al.

It is certified that error appears in the above-identified patent and that said Letters Patent is hereby corrected as shown below:

On the Title Page

Item (71) Applicant reads:
"BÜUK LIMITED"
Should read:
"BÜHLER UK LIMITED"

Signed and Sealed this
Eighth Day of June, 2021

Drew Hirshfeld
*Performing the Functions and Duties of the
Under Secretary of Commerce for Intellectual Property and
Director of the United States Patent and Trademark Office*